(12) United States Patent
Anselmi et al.

(10) Patent No.: US 11,793,738 B2
(45) Date of Patent: Oct. 24, 2023

(54) LIPO-AMINO ACID ALKYL ESTERS AS SPF BOOSTERS

(71) Applicant: Prodotti Gianni S.r.l., Milan (IT)

(72) Inventors: Cecilia Anselmi, Siena (IT); Marisanna Centini, San Quirico d'Orcia (IT); Maria Cristina Giampa, Crotone (IT); Alessandro Sega, Bagno a Ripoli (IT); Giulia Signori, Colle di Val d'Elsa (IT)

(73) Assignee: PRODOTTI GIANNI S.R.L., Milan (IT)

( * ) Notice: Subject to any disclaimer, the term of this patent is extended or adjusted under 35 U.S.C. 154(b) by 0 days.

(21) Appl. No.: 17/544,222

(22) Filed: Dec. 7, 2021

(65) Prior Publication Data
US 2022/0175645 A1 Jun. 9, 2022

(30) Foreign Application Priority Data
Dec. 9, 2020 (IT) .................. 102020000030185

(51) Int. Cl.
*A61K 8/44* (2006.01)
*A61Q 17/04* (2006.01)

(52) U.S. Cl.
CPC ............... *A61K 8/44* (2013.01); *A61Q 17/04* (2013.01)

(58) Field of Classification Search
None
See application file for complete search history.

(56) References Cited

U.S. PATENT DOCUMENTS

| 6,509,008 B1 | 1/2003 | Candau |
| 2005/0065251 A1 | 3/2005 | Candau |
| 2008/0219938 A1 | 9/2008 | Grune |
| 2011/0256076 A1 | 10/2011 | Fletcher |

FOREIGN PATENT DOCUMENTS

| AU | 2009307763 B2 | 10/2015 |
| EP | 2512434 B1 | 11/2016 |
| FR | 2796550 A1 | 1/2001 |
| JP | 5837868 B2 | 12/2015 |
| KR | 101995997 B1 | 7/2019 |
| WO | 2010048124 A3 | 4/2010 |
| WO | 2012161084 A1 | 11/2012 |
| WO | 2015014818 A2 | 2/2015 |
| WO | 2016071336 A1 | 5/2016 |
| WO | 2019022913 A1 | 1/2019 |
| WO | 2020024022 A1 | 2/2020 |
| WO | 2020024023 A1 | 2/2020 |
| WO | 2020041391 A1 | 2/2020 |
| WO | 2020250250 A1 | 12/2020 |

OTHER PUBLICATIONS

Italian Search Report for Italian Application No. IT 202000030185 (2 Pages) (dated Sep. 20, 2021).

*Primary Examiner* — Nannette Holloman
(74) *Attorney, Agent, or Firm* — LUCAS & MERCANTI, LLP (57) ABSTRACT

The use of lipo-amino acid alkyl esters as SPF (Sun Protection Factor) boosters in cosmetic compositions containing a sun filter is described. The alkyl esters, when added to cosmetic compositions containing a sun filter, increase their SPF value by 50% or higher. As a result, the amount of sun filter in the cosmetics can be significantly reduced while maintaining a high SPF. The SPF booster effect was observed in different types of cosmetic compositions and with different sun filters. The alkyl esters have a strong natural connotation and can be obtained by eco-friendly synthesis methods. Photoprotective cosmetic compositions are thereby obtained which are safe to use and have better acceptance by the consumer.

11 Claims, 2 Drawing Sheets

Fig. 2: ¹H-NMR Booster 2

LIPO-AMINO ACID ALKYL ESTERS AS SPF BOOSTERS

CROSS-REFERENCE TO RELATED APPLICATIONS

This application claims the benefit of priority from Italian Patent Application Serial No. 102020000030185 filed on Dec. 9, 2020, the disclosure of which is incorporated herein by reference.

FIELD OF THE INVENTION

The present invention relates to the field of cosmetic products with photoprotective effects and in particular of molecules which are active in increasing photoprotection (SPF boosters).

BACKGROUND OF THE INVENTION

Cosmetic products are applied on the person's surface (skin, keratin, etc.) and are thus normally exposed to solar irradiation. Since solar radiation, in particular ultraviolet radiation, is involved in degradation/aging processes of organic tissues, cosmetic products may include sun filters, namely molecules capable of absorbing and/or reflecting the radiations. These substances prevent aging of organic tissues by cooperating with the specific cosmetic effect of the product which is being used. The use of sun filters is then the rule in the case of cosmetic products specifically intended for photoprotection, such as for example sun creams.

The degree of protection obtained by sun filters and compositions containing them is commonly expressed by the parameter SPF (Sun Protection Factor). It can be defined as the ratio of UV energy required to produce a minimum erythema (Minimum Erythemal Dose, MED) on protected skin, to the corresponding MED on unprotected skin.

The European official method for determining SPF in vivo is reported in EN ISO 24444:2020.

Besides sun filters, molecules active as photoprotection boosters (SPF boosters) are known: these substances are by themselves generally inactive as photoprotectants, but in the presence of a sun filter are capable of increasing its photoprotective activity. Nowadays, the use of boosters has gained particular interest since sun filters are increasingly a discussion topic regarding their safety for human health and their environmental impact. For example, as from Jan. 1, 2020, the ban on selling and using solar products in the Republic of Palau prohibits the use of substances such as Benzophenone-3, Ethylhexyl Methoxycinnamate, 4-Methylbenzylidene Camphor which are deemed to be dangerous for the marine ecosystem (corals). In 2021, Hawaii will prohibit Benzophenone-3 and Ethylhexyl Methoxycinnamate. Searching for substances with boosting effect is thus a new prospect to realize cosmetic products. The search is in particular directed to raw materials capable of exerting synergistic effects with both physical and chemical sun filters, thereby allowing to reduce their concentration in the formula.

SPF boosters can act with different mechanisms. Most of them increase UV absorption and the thickness of the protective film on the skin. Others increase the scattering properties of sun filters, still others enhance UV-A absorption and $\lambda_{cr}$ or improve photostability.

SPF boosters of natural or synthetic origin are known. Among those of natural origin the following can be mentioned: Limnanthantes alba, from which a glucolimnantin-rich product is obtained; essential oils of geranium and calendula; combinations of rutin (Passiflora incarnata L.) and extracts of Plantago lanceolata; licorice roots (Glycyrrhiza inflata); gyrophoric acid, obtained from lichens; algae such as Porphyra umbilicalis (red algae), Haematococcus pluvialis; Dunaliella salina, etc.

Synthetic SPF boosters are known, in particular, from patent literature. In US2008/0219938A1, "Cold Pressed" compositions containing oligosaccharides from Aloe vera and their benefits are reported. Of two patents entitled "Sunscreen composition incorporating methylcellulose as an SPF and/or PPD booster and methods", one (EP2512434B1) reports compositions containing particulate organic filters; the other (US2011/0256076A1; AU2009307763B2) reports compositions comprising metal oxides and methylcellulose.

WO2012/161084A1 describes the booster effect due to scattering of fine porous polyamide particles which have a spherulite structure with an average number of particles having diameter of 1-30 μm and a distribution of 1-2.5. WO2015/014818A2, entitled "Improved sunscreen compositions", describes O/W emulsions containing emulsifiers and filmogenous polymers such as acrylates, crotonates, polyurethanes to increase water resistance and carrageenans (τ or λ).

WO2016/071336A1, entitled "Use of specific acrylates co-polymer as SPF booster", describes a composition comprising selected organic filters (Octocrylene, Avobenzone, Oxybenzone, Octisalate, Homosalate) and a booster based on a polyacrylate-acrylate copolymer with Molecular Weight up to 140000, further comprising mineral UV filter, pigments and nanopigments (e. g. titanium dioxide, zinc oxide, etc.).

A specific booster is reported in WO2019/022913A1 "An SPF booster for use in alcohol base sunscreen formulations", which concerns "multi-stage" polymeric particles consisting of: 1) core, 2) inner shell, 3) outer shell, which can be used in spray products. In JP5837868B2 compositions are found comprising polymeric "UV radiations scatterers", for example: acrylic copolymers/styrene spheres).

Some recent patent applications aim to obtain a high SPF and at the same time a lightening effect (WO2020/024022A1 "Sun care composition for whitening the skin, use of the sun care composition and process of manufacture of the sun care composition") or stability in time and good application properties (texture) (WO2020/024023A1).

Lastly, (WO2020/041391A1 "The methods for protecting and improving the appearance of skin") describes methods for increasing SPF and UVA-PF and at the same time improving skin appearance; the method consists of stratifying on the skin a "perfecting composition" and a solar composition, the order of which is indifferent. The perfecting composition (which includes filmogenous polymers and adhesives and "soft-focus" powders) increases SPF and UVA-PF of the solar composition. If instead the two compositions are pre-mixed and the mixture is applied on the skin, the same SPF booster effect cannot be obtained.

Korean patent KR 10-1995997 reports the booster effect of azelina (a constituent of Nymphaea odorata) and compositions containing organic and inorganic filters and azelina 0.01 to 5% by weight are therein reported. Concentrations lower than 0.01% are not sufficient to have the booster effect and concentrations higher than 5% do not ensure stability of the formulae.

Despite the useful protective effect against solar radiation, SPF boosters are not free of limitations. In particular, natural boosters have issues regarding stability, reproducibility/extent of the effect, cost of gain/purification. Synthetic boosters involve some risks related to the fact that they are not natural and to the possible retaining of traces of toxic reagents used for their synthesis. There is thus a strong need for new substances that can be used as SPF boosters which combine different advantageous properties like the ease of obtainability and/or synthesis; the feature of being very natural; a high efficacy, such as to allow a considerable reduction of the necessary amount of sun filters; an efficacy which is the most independent of the formulation as possible, so as to allow for an easy use in diverse cosmetic compositions, without the need of performing difficult adaptation studies depending on the type of composition. There is also the need for cosmetic compositions with photoprotective effect which are very natural and safe to use, in particular in relation to the photoprotective substances and/or boosters contained therein.

SUMMARY OF THE INVENTION

To address the above-mentioned needs, the present invention concerns the use of lipo-amino acid alkyl esters as Sun Protection Factor (SPF) boosters. It was experimentally observed that the compounds, when added to any cosmetic composition comprising a sun filter, cause an unexpected and considerable increase of the SPF value, even higher than 50%. It is therefore possible to significantly reduce the sun filter amount required for the desired SPF, thereby limiting the environmental impact and possible risks related to prolonged exposure of the consumer to high amount of such substances. The present compounds, being based on amino-acid and lipidic structures, have a strong natural connotation, and are respectful of the organic tissues. In a preferred variant, the same SPF booster of the invention can be obtained by a "green" synthesis method, which is environmentally sound and does not use aggressive reagents which could remain in traces in the final cosmetic product. This further contributes to the natural character and safety of the booster and of the compositions containing the same. As an additional advantage, the booster effect of the present lipo-amino acid alkyl esters was observed on a broad level, that is for many cosmetic compositions different from each other with regard to the type of sun filters used, their amount, excipients, chemical-physical form, and class of the cosmetic product, e.g., emulsions, dispersions, salves, oils, etc. This supports a wide use of the present boosters in any cosmetic composition which is required to have a significant photoprotection level. The invention also includes cosmetic compositions comprising the booster in association with a sun filter.

In accordance with a further aspect of the invention there are provided methods of increasing the Sun Protection Factor (SPF) of a cosmetic product comprising a sun filter. The methods include adding a lipo-amino acid alkyl ester to the cosmetic product. The amount lipo-amino acid alkyl ester added to the cosmetic product containing a sun filter is an amount which is effective, i.e., sufficient, to achieve the desired result.

In yet a still further aspect of the invention there are provided cosmetic products containing an SPF boosting amount of a lipo-amino acid alkyl ester, for example, an amount of between 0.5 and 20% by weight of the cosmetic product is sufficient in most aspects of the invention.

DETAILED DESCRIPTION OF THE INVENTION

According to the present invention, the terms "SPF booster", "photoprotection booster" or simply "booster" refer to a substance which is inactive or scarcely active as a photoprotectant when taken alone, but in the presence of a sun filter, e.g., formulated in a cosmetic composition comprising a sun filter, achieves a significant increase of photoprotection, expressed as SPF. Said increase of photoprotection, in particular the increase of solar protection, is integral part of the present invention and is comprised in the term "SPF booster" used herein.

The expressions "Use of a lipo-amino acid alkyl ester to increase the Sun Protection Factor (SPF)" used herein are equivalent to/interchangeable with "Use of a lipo-amino acid alkyl ester as a SPF booster".

In accordance with one aspect of the invention there are provided methods of increasing the Sun Protection Factor (SPF) of a cosmetic product comprising a sun filter. The methods include adding a lipo-amino acid alkyl ester to the cosmetic product containing the sun filter. The amount lipo-amino acid alkyl ester added to the cosmetic product containing a sun filter is an amount which is effective, i.e. sufficient, to achieve the desired result of boosting the SPF factor of the cosmetic product, and/or reducing the amount of sun filter required to achieve the same SPF effect for the cosmetic. While the amount necessary to achieve the desired result will depend upon the desires of the artisan and the degree of boost desired and the cosmetic product being boosted, one of ordinary skill is able to determine the amount of lipo-amino acid alkyl ester to be included without undue experimentation. For example, the amount of the lipo-amino acid alkyl ester present in the cosmetic product in many embodiments of the invention is an amount of between 0.5 and 20% by weight of the cosmetic product.

The substances used as SPF boosters according to the present invention are lipo-amino acid alkyl esters. "Lipo-amino acid" is herein defined as the amide formed between an amino acid and a fatty acid, and specifically between the amino group of the amino acid and the acyl group of the fatty acid; in the case of amino acids containing more than one amino group (e.g., lysine, histidine) the term lipo-amino acid also applies to said amino acids involved in the corresponding mono- or polyamides as described above.

The amino-acid moiety of the present lipo-amino acids is not subject to particular limitations and may be broadly selected among natural amino acids: alanine, cysteine, aspartic acid, glutamic acid, phenylalanine, glycine, histidine, leucine, isoleucine, lysine, methionine, asparagine, pyrrolysine, proline glutamine, arginine, serine, threonine, selenocysteine, valine, tryptophan, tyrosine, each of the latter being indifferently in L-, D- or racemic form; preferred amino acids according to the invention are non-cyclic amino acids; among them, glycine is particularly preferred. Derivatives of the above-mentioned amino acids or synthesis amino acids (alpha, beta, etc.) may also be used.

The alkyl-ester moiety of the present lipo-amino acid alkyl esters typically consists of a linear or branched alkyl ester $C_{1-24}$, preferably ethyl or methyl, wherein said alkyl ester is formed on the carboxyl group of the lipo-amino acid. If the amino-acid moiety contains more than one carboxyl group, said one or more carboxyl groups may be involved in forming the corresponding mono- or poly-alkyl esters.

The lipidic moiety of the present lipo-amino acids is not subject to particular limitations and is represented by the acyl of any fatty acid, i.e., a linear or branched, saturated or unsaturated, long-chain aliphatic monocarboxylic acid. Typically, the fatty acid is a $C_{4-24}$, a $C_{8-24}$, more preferably a $C_{16-18}$, fatty acid, such as oleic, linoleic, palmitic, stearic acids. It is also possible to use two or more fatty acids, for example a mixture of the fatty acids present in vegetable oils or vegetable butters; examples of vegetable oils are oils of: cashew, peanut, argan, avocado, buriti, coffee, cartamo, coconut, rapeseed, rice bran, corn, macadamia, almonds, walnuts, Brazil nuts, hazelnut, olive, palm, pecan, pistachio nut, sesame, soy, cottonseeds, sunflower seeds, pumpkin seeds, vine seeds, hemp, etc.; according to the invention, preferred oils are oils of: olive, rice bran, buriti, hemp, coffee. Examples of vegetable butters are butter of: cacao bean, shea, cupuaçu, olive, mango, apricot, murumuru, almonds, rice, etc. The term "fatty acid" as defined above is not limited to free fatty acids, but includes also fatty acids which are part of esters and moreover of higher structures, typically (mono-/di-/tri-) glycerides: in this case the amino group of the amino acid will form the amide with an acyl of the corresponding glyceride.

Preferred examples of lipo-amino acid alkyl esters for the use in the present invention are glycine ethyl esters in the form of amide with acyls of: stearic acid, palmitic acid, oleic acid, linoleic acid, fatty acids from vegetable oils (olive, rice bran, buriti, coffee, hemp oils). The amino acid alkyl ester can also be used in the form of the corresponding hydrochloride salt.

The present lipo-amino acid alkyl esters can be produced by synthesis. To this end, it is possible to use: (a) any reaction/process which results in the formation of the amide between the fatty acid and amino acid considered and (b) any reaction/process which results in the formation of the corresponding amino acid alkyl ester. Reactions (a) and (b) may be performed sequentially (the order is indifferent) or simultaneously. Alternatively, it is possible to use an amino acid alkyl ester as a starting material and to form the corresponding lipo-amino acid by reaction (a); or to use a lipo-amino acid as a starting material and to form the corresponding alkyl ester by reaction (b). Preferably, the process is a "green" process, i.e., it is eco-friendly and does not use aggressive chemical reagents which could remain in traces in the final product.

A preferred example of a "green" process is described in the above-mentioned co-pending application PCT/IT2019/000045 in name of the present Applicant, incorporated herein by reference which comprises irradiating with microwaves a mixture comprising: (a) an amino acid alkyl ester and (b) a fatty acid and/or a vegetable oil and/or butter. The amino acid alkyl ester and the fatty acid may be used in a wide range of weight ratios, for example between 1:1 and 1:3; in the case a vegetable oil or butter is used, the weight ratio of the amino acid alkyl ester and the vegetable oil and/or butter may range widely, for example between 0.2:1 and 1:1. The amino acid alkyl ester and the fatty acid or the vegetable oil and/or butter are mixed in a suitable reactor and the mixture is then subjected to microwave irradiation, under stirring.

The reaction results in the formation of an amide between the amino group of the amino acid alkyl ester and the acyl of a fatty acid. The acyl at issue is the one constituting the fatty acid used, in free or esterified form, in particular as a triglyceride when the vegetable oil and/or butter is used. Irradiation is performed obtaining heating of the reaction mixture between 80 and 120° C., for a variable time, for example of 15, 20 or 30 minutes, at room pressure. For the purposes of increasing the reaction yield (understood as the percentage of formation of amide of the amino acid alkyl ester), it is possible to perform the process by subjecting the resulting mixture to one or more further irradiation cycles, for example 2 or 3, in the above-mentioned conditions. Particularly high yields were obtained by two 30-minute process cycles, at 120° C.

Alternatively, or in addition to the application of further cycles, it is also possible to perform further re-cycles: in this case the reaction mixture is first supplemented with new amino acid alkyl ester and then subjected to further irradiation in the above-mentioned conditions. The procedure is repeated depending on the number of re-cycles which are intended to be performed. The reaction may be carried out also in a single cycle by prolonging the irradiation times, depending on the scale-up process. The above-incorporated by reference application PCT/IT2019/000045 also describes examples of lipo-amino acid alkyl esters which can be used in the present invention.

In the present lipo-amino acid alkyl esters, the purity percentage, understood as the amount of amide present in relation to the available amino groups of the amino acid, does not need to be high. It was indeed verified that the SPF booster effect is present also for lipo-amino acids containing significant amounts of non-reacted fatty acid, oil or butter. The products do not entail compatibility problems and can cooperate for the purposes of the invention.

In the present compositions, the sun filter exerts the basal photoprotective action which, according to the invention, is significantly increased by the above-described SPF boosters. It is well known that sun filters protect skin from sun damage and prevent risks of skin cancer such as melanoma and sunburns, early skin aging or sun blotches. Since each sun filter provides a specific kind of protection, sun protection products usually utilize a combination of filters to ensure a broader protection. Combinations of two or more filters are equally usable in the invention and are comprised in the general term "sun filter" used in this description. Sun filters can have an organic or an inorganic structure. Organic filters typically absorb UVA and UVB rays, while inorganic filters (or mineral filters) reflect UVB radiation (titanium dioxide) and UVA radiation (zinc oxide). The sun filters used are those permitted by the legislations of various countries worldwide. In a non-limiting way, they can belong to the following classes: cinnamates (e.g. DEA Methoxycinnamate, Diisopropyl Methyl Cinnamate, Ethyl Diisopropylcinnamate, Ethylhexyl Methoxycinnamate, Glyceryl Ethylhexanoate Dimethoxycinnamate, Isoamyl-p-methoxycinnamate, Isopentyl Trimethoxycinnamate Trisiloxane, Isopropyl Methoxycinnamate, Cinoxate), triazines (e.g. Bis-Ethylhexyloxyphenol Methoxyphenyl Triazine, Tris-Biphenyl Triazine), triazones (e.g. Ethyhexyl Triazone, Diethylhexyl Butamido Triazone), benzimidazoles (e.g. Disodium Phenyl Dibenzimidazole Tetrasulfonate, Phenylbenzimidazole sulphonic acid, Phenylbenzimidazole Sulphonic Acid), camphor derivatives (e.g. 3-Benzilidene Camphor, 4-Methylbenzilidene Camphor, Benzylidene Camphor Sulfonic Acid, Camphor Benzalkonium Methosulphate, Polyacrylamidomethyl Benzylidene Camphor, Terephthalylidene Dicamphor Sulfonic Acid), benzoxazoles, diarylbutadienes, benzotriazoles (e.g. Bisoctrizole, Drometrizole, Drometrizole Trisiloxane), benzylidene malonates, benzal malonates (e.g. Polysilicone 15), salicylates (e.g. Ethyl Salicylate, Isopropylbenzyl Salicylate, Throlamine Salicylate, Homosalate), benzoates (e.g. Diethylamino Hydroxy Benzoyl Hexyl Benzoate, PABA, Ethyl PABA, Butyl PABA, Ethyl Dihydroxypropyl PABA, Ethylhexyl Dimethyl PABA, Glyceryl PABA, Amyl-p-dimethylaminobenzoate, PEG-25 PABA), benzophenones (e.g. Benzophenone 1, Benzophenone 2, Benzophenone 3, Benzophenone 4, Benzophenone 5, Benzophenone 6, Benzophenone 7, Benzophenone 8, Benzophenone-9, 4-propoxy-2-hydroxybenzophenone), dibenzoylmethanes (e.g. Avobenzone), diphenyl acrylates (e.g. Octocrylene), anthranilates (e.g. Menthylantranylate), Ferulic Acid, Digalloyl Trioleate, metal oxides, mixtures of metal oxides with lipids, etc. Particularly preferred are: Bis-Ethylhexyloxyphenol Methoxyphenyl Triazine; Butyl Methoxydibenzoylmethane; Diethylamino Hydroxybenzoyl Hexyl Benzoate; Ethylhexyl Methoxycinnamate; Octocrylene; Titanium Dioxide (And) Caprylic/Capric Triglyceride (And) Alumina (And) Isostearic Acid (And) Polyhydroxystearic Acid (And) Stearic Acid (And) Polyglyceryl-3 Polyricinoleate (And) Lecithin; Titanium Dioxide (and) Silica; Zinc Oxide (And) Caprylic/Capric Triglyceride (And) Polyhydroxystearic Acid (And) Isostearic Acid (And) Lecithin (And) Polyglyceryl-3 Polyricinoleate; Zinc Oxide (and) *Sesamum indicum* (Sesame) Seed Oil (and) Polyglyceryl-2 Dipolyhydroxystearate (and) Polyglyceryl-3 Diisostearate.

The present boosters can be used in any cosmetic product containing a sun filter. The cosmetic product can be broadly selected from: solutions, suspensions, emulsions, gels, hydrogels, creams, unguents, oils, sprays, foams, powders, etc. From an application viewpoint, it can be selected from: skin care products, beauty masks, foundation, powders, talcum powders, soaps, perfumes, eau de toilette, eau de Cologne, preparations for baths and showers, depilation products, deodorants, antiperspirants, hair dyes, hair-waving, -straightening and -fixing products, hair-set products, hair-cleaning products (lotions, powders, shampoo), products to keep hair in shape, hair-styling products (lotions, hair sprays, brilliantines), shaving products, make-up products and make-up-removing products, products intended to be applied on lips, nail care products and nail polishes, sun products, self-tanning products, skin-lightening products and anti-wrinkle products, etc. In a non-limiting variant, the cosmetic composition does not include creams or emulsions or tanning products. In another non-limiting variant, the cosmetic composition is a liquid, creamy or pasty composition. In another non-limiting variant, the cosmetic composition is selected from among emulsions, dispersions, oils, and salves.

In the cosmetic products, the lipo-amino acid alkyl ester can be present in an amount preferably ranging from 0.5 to 20% by weight, more preferably from 0.5 and 15%, of the weight of the composition. The sun filter may be present in an amount ranging from 5 to 80% by weight of the weight of the composition. In particular, the booster effect of the present lipo-amino acid alkyl esters allows to advantageously reduce the amount of sun filter in the more preferred range between 5 and 30% by weight, maintaining high SPF values. It is moreover preferred that there is a balance between the booster and the sun filter. In particular, the weight ratio of the lipo-amino acid alkyl ester to the sun filter can be between 1:0.2 and 1:8.

The invention is now described by the following non-limiting examples.

EXAMPLES

Materials and Methods

Various cosmetic formulations containing physical and chemical filters were prepared, such as: W/O emulsions, O/W emulsions, oily dispersions, sun oils, lip balm.

The filters used for the preparation of the formulations are the following:

Bis-Ethylhexyloxyphenol Methoxyphenyl Triazine;
Butyl Methoxydibenzoylmethane;
Diethylamino Hydroxybenzoyl Hexyl Benzoate;
Ethylhexyl Methoxycinnamate;
Octocrylene;
Titanium Dioxide (And) Caprylic/Capric Triglyceride (And) Alumina (And) Isostearic Acid (And) Polyhydroxystearic Acid (And) Stearic Acid (And) Polyglyceryl-3 Polyricinoleate (And) Lecithin;
Titanium Dioxide (and) Silica;
Zinc Oxide (And) Caprylic/Capric Triglyceride (And) Polyhydroxystearic Acid (And) Isostearic Acid (And) Lecithin (And) Polyglyceryl-3 Polyricinoleate;
Zinc Oxide (and) *Sesamum indicum* (Sesame) Seed Oil (and) Polyglyceryl-2 Dipolyhydroxystearate (and) Polyglyceryl-3 Diisostearate.

Figure 1:
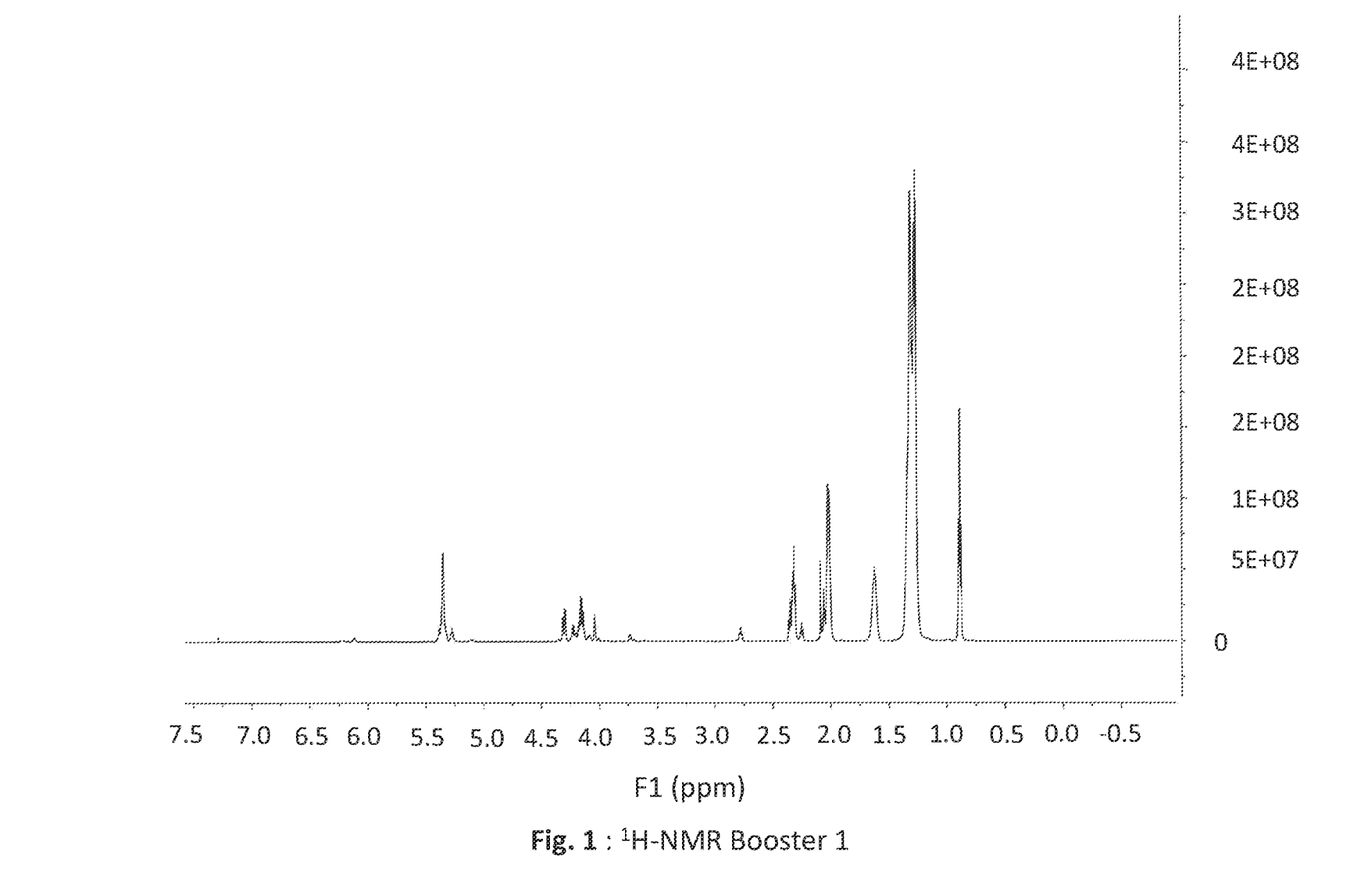
FIG. 1: $^1$H-NMR spectrum of booster 1 used in the present invention.
Figure 2:
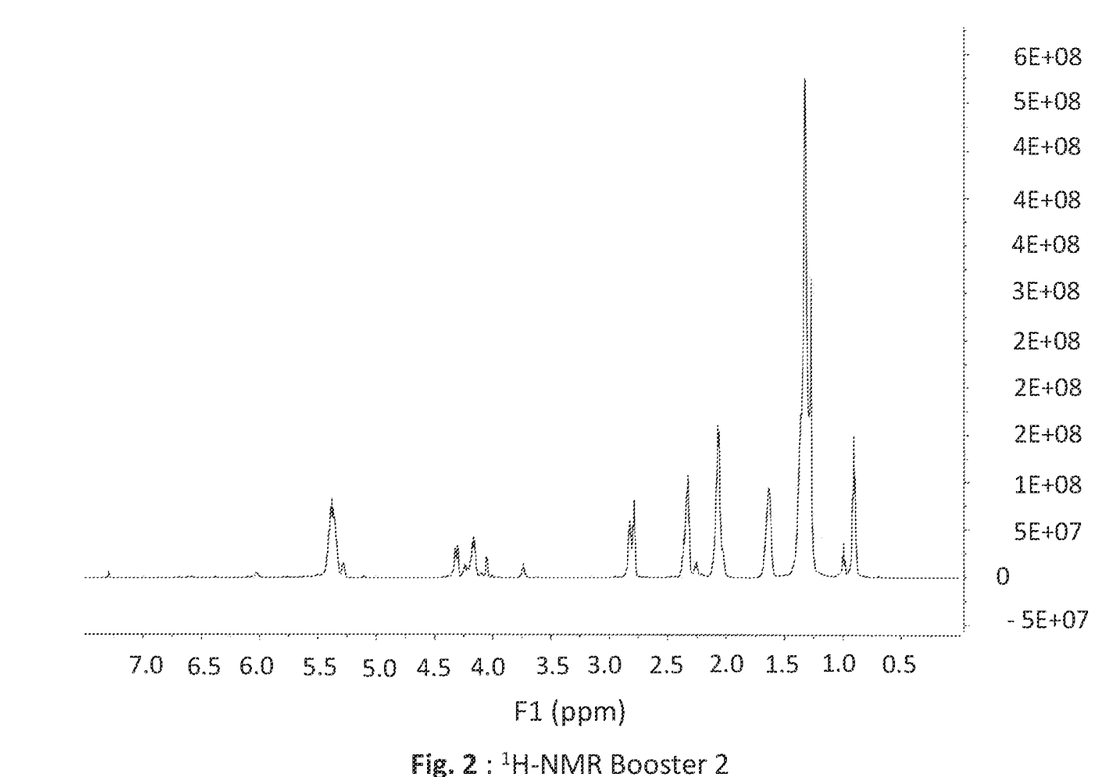
FIG. 2: $^1$H-NMR spectrum of booster 2 used in the present invention.

The booster used is referred to as:

Booster 1 (mixture obtained from olive oil and glycine ethyl ester);
Booster 2 (mixture obtained from hemp oil and glycine ethyl ester);

$^1$H-NMR (600 MHz) spectra of boosters 1 and 2 are shown in FIGS. 1 and 2, respectively. The corresponding values recorded in $CDCl_3$ solvent are reported below.

| PRODUCT | 1H-NMR δ |
|---|---|
| Booster 1 | 0.85-0.90 (t, 3H, R—$CH_3$), 1.20-1.40 (m, —$(CH_2)n$ and $OCH_2CH_3$), 1.6 (m, 2H, $OCOCH_2CH_2$), 2.0 (m, 4H, $CH_2CH$=$CHCH_2$), 2.3 (t, 2H, $OCOCH_2$), 2.75 (t, 2H, $CH$=$CHCH_2CH$=$CH$), 4.05 (d, 2H, $NHCH_2$), 4.15 (dd, 2H, $CH_2O$), 4.22 (q, 2H, $OCH_2CH_3$), 4.30 (dd, 2H, $CH_2O$), 5.25 (m, 1H, CH—O), 5.3-5.4 (m, 2H, —CH=CH—), 6.1 (bp, 1H, NH) |
| Booster 2 | 0.90 (t, 3H, R—$CH_3$), 1.00 (t, 3H, R—$CH_3$ linolenic?) 1.20-1.40 (m, —$(CH_2)n$ and $OCH_2CH_3$), 1.65 (m, 2H, $OCOCH_2CH_2$), 2.05 (m, 4H, $CH_2CH$=$CHCH_2$), 2.35 (m, 2H, $OCOCH_2$—$CH_2$); 2.75-2.85 (m, 2H, —CH=$CHCH_2CH$=CH linoleic and linolenic), 4.1 (d, 2H, $NHCH_2$), 4.2 (m, 2H, $CH_2O$), 4.23 (q, 2H, $OCH_2CH_3$ ethyl), 4.30 (dd, 2H, $CH_2O$), 5.27 (m, 1H, CH=O), 5.45 (m, 2H, —CH=CH—), 6.1 (bp, 1H, NH) |

The amide content is based on the comparison between the integral of the protons of CH$_2$ of glycerol and the integral of the protons of CH$_2$ of the amide.

The CH$_2$ of glycerol is present in all the starting triglyceride molecules: it therefore represents the 100%; if the integral of the CH$_2$ of glycerol is set to 1 (100% starting triglyceride molecules), the integral of the CH$_2$ of the amide directly provides the fraction of molecules with amide chain.

% Amide present in Booster 1: about 50%;

% Amide present in Booster 2: about 36%.

The SPF value was measured according to the following methodology: it was determined in vitro using the spectrophotometer Labsphere 2000S, which is capable of providing data on the basis of the diffuse transmittance of UV radiation across the solar product.

The calculation of the SPF value is in agreement with Diffey's equation (Diffley B., Stokes R. P., Serge F., Mazilier C., Rougier A. *Suncare product photostability: a key parameter for a more realistic in vitro efficacy evaluation. Eur. J. Dermatol.*, 7, 226-228 (1987):

$$SPF = \frac{\sum_{290}^{400} E(\lambda)B(\lambda)}{\sum_{290}^{400} E(\lambda)B(\lambda)T(\lambda)}$$

wherein:

E ($\lambda$) is the spectral solar irradiation;

B ($\lambda$) is the spectrum of erythematous action;

T($\lambda$) is the sample transmittance.

For the determination, PMMA (Poly (Methyl Methacrylate)) in the case of W/O emulsions, dispersions, oils and lip balm; Transpore™ in the case of O/W emulsions were used as substrates.

Cosmetic Formulations

Example 1—W/O Emulsions 1A-1C: W/O emulsions with physical filters (AVERAGE SPF)

| INCI NAME | 1A Booster 0% | 1B Booster 1 5% | 1C Booster 1 10% |
|---|---|---|---|
| Commercial emulsifier | 5 | | |
| Olea Europaea Fruit Oil | 6.5 | 4 | — |
| Copernicia Cerifera Wax | | 1.5 | |
| C12-15 Alkyl Benzoate | | 2 | |
| Helianthus Annuus (Sunflower) Seed Oil | | 2 | |
| Hydrogenated Polyisobutene | 6.5 | 4.5 | 6.5 |
| Tocopherol, Lecithin, Ascorbyl Palmitate, Citric Acid | | 0.05 | |
| Titanium Dioxide (And) Caprylic/Capric Triglyceride (And) Alumina (And) Isostearic Acid (And) Polyhydroxystearic Acid (And) Stearic Acid (And) Polyglyceryl-3 Polyricinoleate (And) Lecithin | | 10 | |
| Zinc Oxide (And) Caprylic/Capric Triglyceride (And) Polyhydroxystearic Acid (And) Isostearic Acid (And) Lecithin (And) Polyglyceryl-3 Polyricinoleate | 10 | | |
| Glyceryl Behenate | | 1.5 | |
| Butyrospermum Parkii (Shea) Butter | | 2 | |
| Theobroma Grandiflorum Seed Butter (And) Tocopherol | | 1 | |
| Polyhydroxystearic Acid (and) Caprylic/Capric Triglyceride (and) Isostearic Acid (and) Lecithin (and) Polyglyceryl-3 Polyricinoleate | | 4 | |
| Booster 1 | — | 5 | 10 |
| Aqua | | q.s. to 100 | |
| Glycerin | | 2.5 | |
| Magnesium Sulfate | | 0.5 | |
| AVERAGE SPF ± STD | 22.78 ± 1.02 | 27.57 ± 1.06 | 28.95 ± 0.98 |

1D-1F: W/O emulsions with physical filters (HIGH SPF)

| INCI NAME | 1D Booster 0% | 1E Booster 1 5% | 1F Booster 1 10% |
|---|---|---|---|
| Commercial emulsifier | 5 | | — |
| Olea Europaea Fruit Oil | 6.5 | 4 | — |
| Copernicia Cerifera Wax | | 1.5 | |
| C12-15 Alkyl Benzoate | | 2 | |
| Helianthus Annuus (Sunflower) Seed Oil | | 2 | |
| Hydrogenated Polyisobutene | 6.5 | 4.5 | 6.5 |
| Tocopherol, Lecithin, Ascorbyl Palmitate, Citric Acid | | 0.05 | |
| Titanium Dioxide (And) Caprylic/Capric Triglyceride (And) Alumina (And) Isostearic Acid (And) Polyhydroxystearic Acid (And) Stearic Acid (And) Polyglyceryl-3 Polyricinoleate (And) Lecithin | | 12.5 | |
| Zinc Oxide (And) Caprylic/Capric Triglyceride (And) Polyhydroxystearic Acid (And) Isostearic Acid (And) Lecithin (And) Polyglyceryl-3 Polyricinoleate | | 15 | |
| Glyceryl Behenate | | 0.5 | |
| Butyrospermum Parkii (Shea) Butter | | 2 | |
| Theobroma Grandiflorum Seed Butter (And) Tocopherol | | 1 | |
| Booster 1 | — | 5 | 10 |
| Aqua | | q.s. to 100 | |
| Glycerin | | 2.5 | |
| Magnesium Sulfate | | 0.5 | |
| AVERAGE SPF ± STD | 40.44 ± 0.95 | 51.53 ± 1.20 | 54.50 ± 0.67 |

| 1G-1J: W/O emulsions with chemical filters (AVERAGE SPF) | | | | |
|---|---|---|---|---|
| | % | | | |
| INCI NAME | 1G Booster 0% | 1H Booster 1 3% | 1I Booster 1 5% | 1J Booster 1 10% |
| Commercial emulsifier | | 5 | | — |
| C12-15 Alkyl Benzoate | 5 | 4 | | 5 |
| Olea Europaea Fruit Oil | 6.5 | 4 | | — |
| Hydrogenated Polyisobutene | 6.5 | 5.5 | | 6.5 |
| Copernicia Cerifera Wax | | 1.5 | | |
| Ethylhexyl Methoxycinnamate | | 3 | | |
| Octocrylene | | 4 | | |
| Bis-Ethylhexyloxyphenol Methoxyphenyl Triazine | | 3 | | |
| Diethylamino Hydroxybenzoyl Hexyl Benzoate | | 3 | | |
| Butyl Methoxydibenzoylmethane | | 2.5 | | |
| Tocopherol, Lecithin, Ascorbyl Palmitate, Citric Acid | | 0.05 | | |
| Glyceryl Behenate | | | | |
| Booster 1 | — | 3 | 5 | 10 |
| Aqua | | q.s. to 100 | | |
| Glycerin | | 4 | | |
| Magnesium Sulfate | | 0.5 | | |
| AVERAGE SPF ± STD | 30.04 ± 0.82 | 37.92 ± 0.61 | 39.97 ± 1.23 | 44.92 ± 0.85 |

| 1K-1O: W/O emulsions with chemical filters (HIGH SPF) | | | | | |
|---|---|---|---|---|---|
| | % | | | | |
| INCI NAME | 1K Booster 0% | 1L Booster 1 5% | 1M Booster 1 10% | 1N Booster 0% | 1O Booster 2 5% |
| Commercial emulsifier | | 5 | — | | 5 |
| C12-15 Alkyl Benzoate | 5 | 4 | 5 | 5 | 4 |
| Olea Europaea Fruit Oil | 6.5 | 4 | — | | |
| Cannabis Sativa Seed Oil | | | | 6.5 | 4 |
| Hydrogenated Polyisobutene | 6.5 | 5.5 | 6.5 | 6.5 | 5.5 |
| Copernicia Cerifera Wax | | 1.5 | | | 1.5 |
| Ethylhexyl Methoxycinnamate | | 5 | | | 5 |
| Octocrylene | | 8 | | | 8 |
| Bis-Ethylhexyloxyphenol Methoxyphenyl Triazine | | 5 | | | 5 |
| Diethylamino Hydroxybenzoyl Hexyl Benzoate | | 3 | | | 3 |
| Butyl Methoxydibenzoylmethane | | 2.5 | | | 2.5 |
| Tocopherol, Lecithin, Ascorbyl Palmitate, Citric Acid | | 0.05 | | | 0.05 |
| Glyceryl Behenate | | 1 | | | 1 |
| Booster 1 | — | 5 | 10 | | |
| Booster 2 | | | | — | 5 |
| Aqua | | q.s. to 100 | | | q.s. to 100 |
| Glycerin | | 4 | | | 4 |
| Magnesium Sulfate | | 0.5 | | | 0.5 |
| AVERAGE SPF ± STD | 51.03 ± 0.94 | 63.57 ± 0.46 | 69.81 ± 0.98 | 52.00 ± 0.90 | 57.03 ± 0.33 |

Example 2—O/W Emulsions

2A-2C: O/W emulsions with chemical and physical filters (Booster 1)

| INCI NAME | 2A Booster 0% | 2B Booster 1 3% | 2C Booster 1 5% |
|---|---|---|---|
| Cetearyl Alcohol (and) Cetearyl Glucoside | 5 | | |
| Ethylhexyl Methoxycinnamate | 6.5 | | |
| Butyl Methoxydibenzoylmethane | 2 | | |
| Ethylhexyl Salicylate | 4 | | |
| Octocrylene | 4 | | |
| Titanium Dioxide (and) Silica | 2 | | |
| Cetearyl isononanoate | 2 | | |
| C12-15 Alkyl Benzoate | 12 | | 10 |
| Dicaprylyl Ether | 4.50 | | 4 |
| Olea Europaea Fruit Oil | 2.5 | | — |
| Lecithin, Tocopherol, Ascorbyl palmitate, Citric acid | | 0.05 | |
| Booster 1 | — | 3 | 5 |
| Aqua | | q.s. to 100 | |
| Glycerin | | 4 | |
| Disodium EDTA | | 0.15 | |
| Potassium Cetyl Phosphate | | 0.2 | |
| Benzyl Alcohol (and) Ethylhexylglycerin (and) Tocopherol | | 1 | |
| AVERAGE SPF ± STD | 27.80 ± 0.44 | 35.51 ± 0.1 | 38.71 ± 0.62 |

2D-2E: O/W emulsions with chemical and physical filters (Booster 2)

| INCI NAME | 2D Booster 0% | 2E Booster 2 5% |
|---|---|---|
| Cetearyl Alcohol (and) Cetearyl Glucoside | 5 | |
| Ethylhexyl Methoxycinnamate | 6.5 | |
| Butyl Methoxydibenzoylmethane | 2 | |
| Ethylhexyl Salicylate | 4 | |
| Octocrylene | 4 | |
| Titanium Dioxide (and) Silica | 2 | |
| Cetearyl isononanoate | 2 | |
| C12-15 Alkyl Benzoate | 12 | 10 |
| Dicaprylyl Ether | 4.50 | 4 |
| Cannabis Sativa Seed Oil | 2.5 | — |
| Lecithin, Tocopherol, Ascorbyl palmitate, Citric acid | 0.05 | |
| Booster 2 | — | 5 |
| Aqua | q.s. to 100 | |
| Glycerin | 4 | |
| Disodium EDTA | 0.15 | |
| Potassium Cetyl Phosphate | 0.2 | |
| Benzyl Alcohol (and) Ethylhexylglycerin (and) Tocopherol | 1 | |
| AVERAGE SPF ± STD | 27.14 ± 0.89 | 32.66 ± 1.19 |

2F-2G: Commercial O/W Emulsion (Booster 1)

The addition of the Booster mixture 1 to a commercial product formulated as an emulsion with high SPF was also evaluated.

Hereinafter, the composition of INCI ingredients as on the package is reported. Also in this case, the booster addition causes an increase of SPF in vitro.

Ingredients: Aqua, Homosalate, Ethylhexyl Salicylate, Glycerin, Caprylyl Caprylate/Caprate, Butyl Methoxydibenzoylmethane, Dimethicone, Bis-Ethylhexyloxyphenol Methoxyphenyl Triazine, Methylene Bis-Benzotriazolyl Tetramethylbutylphenol (Nano), Tris-Biphenyl Triazine (Nano), Potassium Cetyl Phosphate, Propylheptyl Caprylate, Sodium Hyaluronate, Butylene Glycol, Caprylyl Glycol, Carbomer, Cetyl Alcohol, Citric Acid, Decyl Glucoside, Dimethicone/Vinyl Dimethicone Crosspolymer, Disodium Phosphate, Hydrogenated Dimer Dilinoleyl/Dimethylcarbonate Copolymer, Parfum, PEG-8 Laurate, Pentaerythrityl Tetra-Di-T-Butyl Hydroxyhydrocinnamate, Phenoxyethanol, Polyacrylate Crosspolymer-6, Polymethyl Methacrylate, Propylene Glycol, Silica Sodium Dehydroacetate, Styrene/Acrylates Copolymer, T-Butyl Alcohol, Tapioca Starch, Tocopheryl Acetate, Trisodium Ethylenediamine Disuccinate, Xanthan Gum.

SPF EMULSION: 35.01±0.57

SPF EMULSION with addition of BOOSTER 1 MIXTURE 5%: 45.98±0.34

Example 3—Dispersions 3A-3F: Dispersions with Physical Filters (AVERAGE SPF)

Dispersions with two mixtures of different physical filters were evaluated. The formulations are reported below.

| INCI NAME | 3A Booster 0% | 3B Booster 1 5% |
|---|---|---|
| Dicaprylyl Carbonate | 30.95 | 29.7 |
| Caprylic/Capric Triglyceride | 26.95 | 25.7 |
| Argania Spinosa Kernel Oil | | 5 |
| Helianthus Annuus (Sunflower) Seed Oil | | 2 |
| Olea Europaea Fruit Oil | 2.5 | — |
| Glyceryl Behenate | | 5 |
| Titanium Dioxide (And) Caprylic/Capric Triglyceride (And) Alumina (And) Isostearic Acid (And) Polyhydroxystearic Acid (And) Stearic Acid (And) Polyglyceryl-3 Polyricinoleate (And) Lecithin | 12.5 | |
| Zinc Oxide (And) Caprylic/Capric Triglyceride (And) Polyhydroxystearic Acid (And) Isostearic Acid (And) Lecithin (And) Polyglyceryl-3 Polyricinoleate | 15 | |
| Booster 1 | — | 5 |
| Tocopherol | | 0.1 |
| AVERAGE SPF ± STD | 19.61 ± 0.32 | 30.24 ± 0.48 |

| INCI NAME | 3C Booster 0% | 3D Booster 1 5% |
|---|---|---|
| Dicaprylyl Carbonate | 47.75 | 46.55 |
| Caprylic/Capric Triglyceride | 26.65 | 25.35 |
| Argania Spinosa Kernel Oil | | 5 |
| Helianthus Annuus (Sunflower) Seed Oil | | 2 |
| Olea Europaea Fruit Oil | 2.5 | — |
| Titanium Dioxide (and) Silica | | 13 |

-continued

| INCI NAME | 3C Booster 0% | 3D Booster 1 5% |
|---|---|---|
| Zinc Oxide (and) Sesamum Indicum (Sesame) Seed Oil (and) Polyglyceryl-2 Dipolyhydroxystearate (and) Polyglyceryl-3 Diisostearate | 3 | |
| Booster 1 | — | 5 |
| Tocopherol | 0.1 | |
| AVERAGE SPF ± STD | 24.00 ± 0.54 | 32.58 ± 0.35 |

| INCI NAME | % 3E Booster 0% | 3F Booster 2 5% |
|---|---|---|
| Dicaprylyl Carbonate | 30.95 | 29.7 |
| Caprylic/Capric Triglyceride | 26.95 | 25.7 |
| Argania Spinosa Kernel Oil | 5 | |
| Helianthus Annuus (Sunflower) Seed Oil | 2 | |
| Cannabis Sativa Seed Oil | 2.5 | — |
| Glyceryl Behenate | 5 | |
| Titanium Dioxide (And) Caprylic/Capric Triglyceride (And) Alumina (And) Isostearic Acid (And) Polyhydroxystearic Acid (And) Stearic Acid (And) Polyglyceryl-3 Polyricinoleate (And) Lecithin | 12.5 | |
| Zinc Oxide (And) Caprylic/Capric Triglyceride (And) Polyhydroxystearic Acid (And) Isostearic Acid (And) Lecithin (And) Polyglyceryl-3 Polyricinoleate | 15 | |
| Booster 2 | — | 5 |
| Tocopherol | 0.1 | |
| AVERAGE SPF ± STD | 18.83 ± 0.49 | 24.04 ± 0.37 |

3G-3H: Commercial Dispersion (Booster 1)

The addition of the Booster 1 mixture to a commercial product formulated as a dispersion with high SPF was also evaluated.

Hereinafter, the composition of INCI ingredients as on the package is reported. Also in this case, the booster addition causes an increase of SPF in vitro.

INGREDIENTS: Dicaprylyl Carbonate, Caprylic/Capric Triglyceride, Titanium Dioxide, Argania Spinosa Kernel Oil, Aluminum Hydroxide, Stearic Acid, Polyglyceryl-3 Diisostearate, Oleyl Alcohol, Zanthoxylum Alatum Fruit Extract, Helianthus Annuus Hybrid Oil, *Olea Europaea* (Olive) Fruit Oil, Propolis Extract, Pollen Extract SPF COMMERCIAL DISPERSION: 52.37±0.63
SPF COMMERCIAL DISPERSION with addition of BOOSTER 1 MIXTURE 5%: 67.81±1.00

Example 4—Sun Oil 4A-4C: Sun oil (Booster 1)

| INCI NAME | 4A Booster 0% | 4B Booster 1 3% | 4C Booster 1 5% |
|---|---|---|---|
| Dicaprylyl Carbonate | 25 | | 23.75 |
| Caprylic/Capric Triglyceride | 27 | | 25.75 |
| Hydrogenated Polyisobutene | | 22.9 | |
| Isoamyl Laurate | | 5 | |
| Olea Europaea Fruit Oil | 2.5 | — | |
| Dicaprylyl Ether | | 5 | |
| Bis-Ethylhexyloxyphenol Methoxyphenyl Triazine | | 3 | |
| Ethylhexyl Methoxycinnamate | | 5 | |
| Butyl Methoxydibenzoylmethane | | 2.5 | |
| Diethylamino Hydroxybenzoyl Hexyl Benzoate | | 2 | |
| Booster 1 | — | 3 | 5 |
| Tocopherol | 0.1 | | |
| AVERAGE SPF ± STD | 22.38 ± 0.56 | 28.01 ± 0.27 | 31.58 ± 0.45 |

4D-4E: Sun oil (Booster 2)

| INCI NAME | 4D Booster 0% | 4E Booster 2 5% |
|---|---|---|
| Dicaprylyl Carbonate | 25 | 23.75 |
| Caprylic/Capric Triglyceride | 27 | 25.75 |
| Hydrogenated Polyisobutene | | 22.9 |
| Isoamyl Laurate | | 5 |
| Cannabis Sativa Seed Oil | 2.5 | — |
| Dicaprylyl Ether | | 5 |
| Bis-Ethylhexyloxyphenol Methoxyphenyl Triazine | | 3 |
| Ethylhexyl Methoxycinnamate | | 5 |
| Butyl Methoxydibenzoylmethane | | 2.5 |
| Diethylamino Hydroxybenzoyl Hexyl Benzoate | | 2 |
| Booster 2 | — | 5 |
| Tocopherol | 0.1 | |
| AVERAGE SPF ± STD | 24.51 ± 0.34 | 29.50 ± 0.50 |

Example 5—Lip Balm 5A-5B: Lip balm with physical filters

| INCI NAME | 5A Booster 0% | 5B Booster 1 5% |
|---|---|---|
| *Copernicia Cerifera* Wax | | 2.5 |
| *Euphorbia Cerifera* Wax | | 7 |
| Hydrogenated Olive Oil Stearyl Esters | | 8 |
| *Theobroma Grandiflorum* Seed Butter | | 6 |
| *Theobroma Cacao* Butter | | 7 |
| *Butyrospermum Parkii* (Shea) Butter | | 3 |
| Glyceryl Behenate | | 3 |
| Tocopherol | | 0.1 |
| *Olea Europaea* Fruit Oil | 2.5 | — |
| *Limnanthes Alba* (Meadowfoam) Seed Oil | | 8 |
| *Helianthus Annuus* (Sunflower) Seed Oil | | 4 |
| *Prunus Amygdalus Dulcis* Oil | | 9.2 |
| *Ricinus Communis* (Castor) Seed Oil | 15 | 12.5 |
| *Simmondsia Chinensis* (Jojoba) Seed Oil | | 7 |

| 5A-5B: Lip balm with physical filters | | |
|---|---|---|
| | % | |
| INCI NAME | 5A Booster 0% | 5B Booster 1 5% |
| Hydrogenated Polyisobutene | 7.7 | |
| Booster 1 | — | 5 |
| Titanium Dioxide (And) Caprylic/Capric Triglyceride (And) Alumina (And) Isostearic Acid (And) Polyhydroxystearic Acid (And) Stearic Acid (And) Polyglyceryl-3 Polyricinoleate (And) Lecithin | 5 | |
| Zinc Oxide (And) Caprylic/Capric Triglyceride (And) Polyhydroxystearic Acid (And) Isostearic Acid (And) Lecithin (And) Polyglyceryl-3 Polyricinoleate | 5 | |
| AVERAGE SPF ± STD | 16.18 ± 0.34 | 25.36 ± 0.52 |

| 5C-5D: Lip balm with chemical filters | | |
|---|---|---|
| | % | |
| INCI NAME | 5C Booster 0% | 5D Booster 1 5% |
| Copernicia Cerifera Wax | 2.5 | |
| Euphorbia Cerifera Wax | 8 | |
| Hydrogenated Olive Oil Stearyl Esters | 8 | |
| Theobroma Grandiflorum Seed Butter | 6 | |
| Theobroma Cacao Butter | 8 | |
| Butyrospermum Parkii (Shea) Butter | 3 | |
| Glyceryl Behenate | 4 | |
| Tocopherol | 0.1 | |
| Olea Europaea Fruit Oil | 2.5 | — |
| Limnanthes Alba (Meadowfoam) Seed Oil | 8 | |
| Helianthus Annuus (Sunflower) Seed Oil | 2 | |
| Prunus Amygdalus Dulcis Oil | 9.2 | |
| Ricinus Communis (Castor) Seed Oil | 17.5 | 15 |
| Simmondsia Chinensis (Jojoba) Seed Oil | 7 | |
| Hydrogenated Polyisobutene | 7.7 | |
| Booster 1 | — | 5 |
| Ethylhexyl Methoxycinnamate | 4 | |
| Butyl Methoxydibenzoylmethane | 2.5 | |
| AVERAGE SPF ± STD | 13.34 ± 0.79 | 21.96 ± 1.04 |

Summary of Results

Hereinafter, the results obtained in the various examples above are summarized below.

The tables show: the formulation examples with indication of the amounts of booster and filters used, the SPF value obtained and the percentage of increase of the SPF value due to the booster.

Example 1—W/O Emulsions

| EXAMPLE | | % FILTERS USED | | AVERAGE SPF ± STD | SPF % INCREASE |
|---|---|---|---|---|---|
| | | AVERAGE SPF | | | |
| 1A | Booster: 0% | Titanium Dioxide | 10 | 22.78 ± 1.02 | — |
| 1B | Booster 1: 5% | (And) Caprylic/Capric | | 27.57 ± 1.06 | 21.03% |
| 1C | Booster 1: 10% | Triglyceride (And) Alumina (And) Isostearic Acid (And) Polyhydroxystearic Acid (And) Stearic Acid (And) Polyglyceryl-3 Polyricinoleate (And) Lecithin | | 28.95 ± 0.98 | 27.08% |
| | | Zinc Oxide (And) Caprylic/Capric Triglyceride (And) Polyhydroxystearic Acid (And) Isostearic Acid (And) Lecithin (And) Polyglyceryl-3 Polyricinoleate | 10 | | |
| | | HIGH SPF | | | |
| 1D | Booster: 0% | Titanium Dioxide | 12.5 | 40.44 ± 0.95 | — |
| 1E | Booster 1: 5% | (And) Caprylic/Capric | | 51.53 ± 1.20 | 27.42% |
| 1F | Booster 1: 10% | Triglyceride (And) Alumina (And) Isostearic Acid (And) Polyhydroxystearic Acid (And) Stearic | | 54.50 ± 0.67 | 34.77% |

-continued

| EXAMPLE | % FILTERS USED | | AVERAGE SPF ± STD | SPF % INCREASE |
|---|---|---|---|---|
| | Acid (And) Polyglyceryl-3 Polyricinoleate (And) Lecithin | | | |
| | Zinc Oxide (And) Caprylic/Capric Triglyceride (And) Polyhydroxystearic Acid (And) Isostearic Acid (And) Lecithin (And) Polyglyceryl-3 Polyricinoleate | 15 | | |

W/O Emulsions Containing Chemical Filters

| EXAMPLE | | % FILTERS USED | | AVERAGE SPF ± STD | SPF % INCREASE |
|---|---|---|---|---|---|
| | | AVERAGE SPF | | | |
| 1G | Booster: 0% | Ethylhexyl Methoxycinnamate | 3 | 30.04 ± 0.82 | — |
| 1H | Booster 1: 3% | Octocrylene | 4 | 37.92 ± 0.61 | 26.23% |
| 1I | Booster 1: 5% | Bis-Ethylhexyloxyphenol | 3 | 39.97 ± 1.23 | 33.05% |
| 1J | Booster 1: 10% | Methoxyphenyl Triazine | | 44.92 ± 0.85 | 49.53% |
| | | Diethylamino Hydroxybenzoyl Hexyl Benzoate | 3 | | |
| | | Butyl Methoxydibenzoylmethane | 2.5 | | |
| | | HIGH SPF | | | |
| 1K | Booster: 0% | Ethylhexyl Methoxycinnamate | 5 | 51.03 ± 0.94 | — |
| 1L | Booster 1: 5% | Octocrylene | 8 | 63.57 ± 0.46 | 24.57% |
| 1M | Booster 1: 10% | Bis-Ethylhexyloxyphenol | 5 | 69.81 ± 0.98 | 36.8% |
| 1N | Booster: 0% | Methoxyphenyl Triazine | | 52.00 ± 0.90 | — |
| 1O | Booster 2: 5% | Diethylamino Hydroxybenzoyl Hexyl Benzoate | 3 | 57.03 ± 0.33 | 9.67% |
| | | Butyl Methoxydibenzoylmethane | 2.5 | | |

Example 2—O/W Emulsions

| EXAMPLE | | % FILTERS USED | | AVERAGE SPF ± STD | SPF % INCREASE |
|---|---|---|---|---|---|
| 2A | Booster: 0% | Ethylhexyl Methoxycinnamate | 6.54 | 27.80 ± 0.44 | — |
| 2B | Booster 1: 3% | Octocrylene | 4 | 35.51 ± 0.10 | 27.73% |
| 2C | Booster 1: 5% | Butyl Methoxydibenzoylmethane | 2 | 38.71 ± 0.62 | 39.24% |
| 2D | Booster: 0% | Ethylhexyl Salicylate | 4 | 27.14 ± 0.89 | — |
| 2E | Booster 2: 5% | Titanium Dioxide and Silica | 2 | 32.66 ± 1.19 | 20.33% |

Commercial O/W Emulsion

| EXAMPLE | COMPOSITION | FILTERS USED | AVERAGE SPF ± STD | SPF % INCREASE |
|---|---|---|---|---|
| 2F | Booster: 0% | Homosalate, Ethylhexyl Salicylate, Butyl Methoxydibenzoylmethane, Bis-Ethylhexyloxyphenol Methoxyphenyl Triazine, Methylene Bis-Benzotriazolyl Tetramethylbutylphenol (Nano), Tris-Biphenyl Triazine (Nano) | 35.01 ± 0.57 | — |
| 2G | Booster 1: 5% | | 45.98 ± 0.34 | 31.33% |

Example 3—Oily Dispersions

| EXAMPLE | | % FILTERS USED | | AVERAGE SPF ± STD | SPF % INCREASE |
|---|---|---|---|---|---|
| 3A | Booster: 0% | Titanium Dioxide (And) Caprylic/Capric Triglyceride (And) Alumina (And) Isostearic Acid (And) Polyhydroxysteari Acid (And) Stearic Acid (And) Polyglyceryl-3 Polyricinoleate (And) Lecithin | 12.5 | 19.61 ± 0.32 | — |
| 3B | Booster 1: 5% | | | 30.24 ± 0.48 | 54.20% |
| | | Zinc Oxide (And) Caprylic/Capric Triglyceride (And) Polyhydroxystearic Acid (And) Isostearic Acid (And) Lecithin (And) Polyglyceryl-3 Polyricinoleate | 15 | | |
| 3C | Booster 0% | Titanium Dioxide (and) Silica | 13 | 24.00 ± 0.54 | — |
| 3D | Booster 1: 5% | Zinc Oxide (and) *Sesamum Indicum* (Sesame) Seed Oil (and) Polyglyceryl-2 Dipolyhydroxystearate (and) Polyglyceryl-3 Diisostearate | 3 | 32.58 ± 0.35 | 35.75% |
| 3E | Booster: 0% | Titanium Dioxide (And) Caprylic/Capric Triglyceride (And) Alumina (And) Isostearic Acid (And) Polyhydroxystearic Acid (And) Stearic Acid (And) Polyglyceryl-3 Polyricinoleate (And) Lecithin | 12.5 | 18.83 ± 0.49 | — |
| 3F | Booster 2: 5% | | | 24.04 ± 0.37 | 27.67% |
| | | Zinc Oxide (And) Caprylic/Capric Triglyceride (And) Polyhydroxystearic Acid (And) Isostearic Acid (And) Lecithin (And) Polyglyceryl-3 Polyricinoleate | 15 | | |

Commercial Dispersion

| EXAMPLE | | FILTERS USED | AVERAGE SPF ± STD | SPF % INCREASE |
|---|---|---|---|---|
| 3G | Booster: 0% | Titanium Dioxide | 52.37 ± 0.63 | — |
| 3H | Booster 1: 5% | | 67.81 ± 1.00 | 29.48% |

Example 4—Sun Oils

| EXAMPLE | | % FILTERS USED | | AVERAGE SPF ± STD | SPF % INCREASE |
|---|---|---|---|---|---|
| 4A | Booster: 0% | Ethylhexyl Methoxycinnamate | 5 | 22.38 ± 0.56 | — |
| 4B | Booster 1: 3% | Bis-Ethylhexyloxyphenol | 3 | 28.01 ± 0.27 | 25.15% |
| 4C | Booster 1: 5% | Methoxyphenyl Triazine | | 31.58 ± 0.45 | 41.11% |
| 4D | Booster 0% | Diethylamino Hydroxybenzoyl | 2 | 24.51 ± 0.34 | — |
| 4E | Booster 2: 5% | Hexyl Benzoate | | 29.50 ± 0.50 | 20.36% |
| | | Butyl Methoxydibenzoylmethane | 2.5 | | |

Example 5—Lip Balm

| EXAMPLE | | % FILTERS USED | | AVERAGE SPF ± STD | SPF % INCREASE |
|---|---|---|---|---|---|
| 5A | Booster: 0% | Titanium Dioxide (And) Caprylic/Capric Triglyceride (And) Alumina (And) Isostearic Acid (And) Polyhydroxystearic Acid (And) Stearic Acid (And) Polyglyceryl-3 Polyricinoleate (And) Lecithin | 5 | 16.18 ± 0.34 | — |
| 5B | Booster 1: 5% | | | 25.36 ± 0.52 | 56.74% |
| | | Zinc Oxide (And) Caprylic/Capric Triglyceride (And) Polyhydroxystearic Acid (And) Isostearic Acid (And) Lecithin (And) Polyglyceryl-3 Polyricinoleate | 5 | | |

Lip Balm with Chemical Filters

| EXAMPLE | | % FILTERS USED | | AVERAGE SPF ± STD | SPF % INCREASE |
|---|---|---|---|---|---|
| 5C | Booster: 0% | Butyl Methoxydibenzoylmethane | 2.5% | 13.34 ± 0.79 | — |
| 5D | Booster 1: 5% | Ethylhexyl Methoxycinnamate | 4 | 21.96 ± 1.04 | 64.62% |

Synthesis of Lipo-Amino Acid Alkyl Esters

1. Materials and Methods

Glycine ethyl ester was chosen as working example. The synthesis was carried out with microwave irradiation, in the absence of organic solvents. Yields and yield differences were evaluated using fatty acids or, as an alternative, vegetable oils as a reagent. Reaction yields were evaluated as a percentage of amide in the reaction raw material after washing with water.

Method 1: Temperature 120° C.; Oil: Amino acid ester ratio=5:1 (i.e., 1:0.2) by weight; microwave (MW) irradiation: 60' (two cycles of 30' duration each).

Method 2: Temperature 120° C.; Oil: Amino acid ester (hydrochloride) ratio=5:1 by weight; Amino acid ester (hydrochloride):Sodium acetate ratio=1:1 molar.

MW irradiation: 60' (two cycles of 30' duration each)

| Oil used | Method of synthesis MW Irr. | Yield % | Method of analysis | Product appearance |
|---|---|---|---|---|
| Olive oil | i, 2 × 30-min recycles | 16.91 | HPLC | Yellow-orange liquid |
| Rice bran oil | i, 2 × 30-min recycles | 26.15 | HPLC | Orange liquid |
| Buriti oil | i, 2 × 30-min recycles | 33.11 | HPLC | Red liquid |
| Olive oil | i, 10 min | 6.36 | HPLC | Yellow-orange liquid |
| Olive oil | i, 20 min | 8.40 | CC* | Yellow-orange liquid |
| | | 7.76 | HPLC | |
| Olive oil | i, 30 min | 11.94 | CC | Yellow-orange liquid |
| | | 9.15 | HPLC | |
| Olive oil | i, 2 × 20-min recycles | 11.90 | HPLC | Yellow-orange liquid |
| Rice bran oil | i, 2 × 20-min recycles | 18.67 | HPLC | Orange liquid |
| Rice bran oil | i, 3 × 20-min recycles | 25.50 | HPLC | Orange liquid |
| Olive oil | i, 3 × 20-min recycles | 41.30 | HPLC | Yellow-orange liquid |

*CC: Chromatographic Column

Purification allowed the separation of a secondary product (dipeptide by-product) characterized by NMR, of formula (I), where R corresponds to the alkyl radical of the fatty acid.

(I)

Characterization:

The reaction products, both as raw materials (after washing with water) and as pure products (after purification with Layer or Column Chromatography), were analyzed with $^1$H-NMR.

HPLC analysis allowed to identify and quantify the amides of oleic and linoleic acids. The differences in the yields between the two amides reflect the percentage of the acidic components in the starting oils. The synthesized compounds have lipophilic characteristics.

TABLE 1

Chemical shifts of some of the pure amides obtained with fatty acids and with oils

| PRODUCT | 1H NMR δ |
|---|---|
| Pure amide from fatty acids of olive oil | 0.85 (t, 3H, —CH$_3$); 1.18-1.40 (bp, nH, —(CH$_2$)$_n$ and —OCH$_2$CH$_3$); 1.62 (bp, 2H, —COCH$_2$CH$_2$—); 2.01 (m, 4H, —CH$_2$CH=CHCH$_2$—); 2.22 (t, 2H, —HNCOCH$_2$—); 2.76 (t, 2H, —CH=CHCH$_2$CH=CH—); 4.02 (d, 2H, —OCOCH$_2$NHCO—); 4.22 (q, 2H, —OCH$_2$CH$_3$); 5.33 (bp, 2H, —CH=CH—); 5.91 (bp, 1H, NH). |
| Pure amide from oleic acid | 0.86 (t, 3H, —CH$_3$); 1.23-1.29 (bp, nH, —(CH$_2$)$_n$ and —OCH$_2$CH$_3$); 1.61 (bp, 2H, —COCH$_2$CH$_2$—); 1.99 (m, 4H, —CH$_2$CH=CHCH$_2$—); 2.21 (t, 2H, —HNCOCH$_2$—); 2.75 (t, 2H, —CH=CHCH$_2$CH=CH—); 4.02 (d, 2H, —OCOCH$_2$NHCO—); 4.20 (q, 2H, —OCH$_2$CH$_3$); 5.31 (bp, 2H, —CH=CH—); 5.89 (bp, 1H, NH). |
| Pure amide from olive oil | 0.86 (t, 3H, —CH$_3$); 1.15-1.40 (bp, nH, —(CH$_2$)$_n$ and —OCH$_2$CH$_3$); 1.61 (bp, 2H, —COCH$_2$CH$_2$); 1.99 (m, 4H, —CH$_2$CH=CHCH$_2$—); 2.21 (t, 2H, —HNCOCH$_2$—); 2.75 (t, 2H, —CH=CHCH$_2$CH=CH—); 4.02 (d, 2H, —OCOCH$_2$NHCO—); 4.21 (q, 2H, —OCH$_2$CH$_3$); 5.35 (bp, 2H, —CH=CH—); 5.90 (bp, 1H, NH). |
| Pure amide from rice bran oil | 0.86 (t, 3H, —CH$_3$); 1.23-1.27 (bp, nH, —(CH$_2$)$_n$ and —OCH$_2$CH$_3$); 1.61 (bp, 2H, —COCH$_2$CH$_2$—); 1.99 (m, 4H, —CH$_2$CH=CHCH$_2$—); 2.21 (t, 2H, —HNCOCH$_2$—); 2.74 (t, 2H, —CH=CHCH$_2$CH=CH—); 4.00 (d, 2H, —OCOCH$_2$NHCO—); 4.19 (q, 2H, —OCH$_2$CH$_3$); 5.32 (bp, 2H, —CH=CH—); 5.97 (bp, 1H, NH). |
| Pure amide from coffee oil | 0.87 (t, 3H, —CH$_3$); 1.23-1.29 (bp, nH, —(CH$_2$)$_n$ and —OCH$_2$CH$_3$); 1.62 (bp, 2H, —COCH$_2$CH$_2$—); 2.02 (m, 4H, —CH$_2$CH=CHCH$_2$—); 2.21 (t, 2H, —HNCOCH$_2$—); 2.75 (t, 2H, —CH=CHCH$_2$CH=CH—); 4.02 (d, 2H, —OCOCH$_2$NHCO—); 4.20 (q, 2H, —OCH$_2$CH$_3$); 5.33 (bp, 2H, —CH=CH—); 5.90 (bp, 1H, NH). |

TABLE 2

Chemical shifts of the amide (by product) obtained from oleic acid

| PRODUCT | MOLECULAR STRUCTURE |
|---|---|
| Second amide from olive oil | R—C(=O)—NH—CH$_2$—C(=O)—NH—CH$_2$—COOCH$_2$CH$_3$ |

1H NMR δ

0.87 (t, 3H, —CH$_3$); 1.23-1.29 (bp, nH, —(CH$_2$)$_n$ e —OCH$_2$CH$_3$); 1.62 (bp, 2H, —COCH$_2$CH$_2$—); 2.02 (m, 4H, —CH$_2$CH=CHCH$_2$—); 2.22 (t, 2H, —HNCOCH$_2$—); 2.31 (t, 2H, —OHCOCH$_2$—); 2.75 (t, 2H, —CH=CHCH$_2$CH=CH—); 3.97 (d, 2H, —CONHCH$_2$CONHCH$_2$COO—); 4.02 (d, 2H, —CONHCH$_2$CONHCH$_2$COO—); 5.33 (bp, 2H, —CH=CH—); 6.12 (bp, 1H, —CONHCH$_2$CONHCH$_2$COO—); 6.43 (bp, 1H, —CONHCH$_2$CONHCH$_2$COO—).

TABLE 3

Chemical shifts of the raw products after washing with water

| PRODUCT | 1H NMR δ |
|---|---|
| Raw material from olive fatty acids | 0.85 (t, 3H, —CH$_3$); 1.18-1.40 (bp, nH, —(CH$_2$)$_n$ and —OCH$_2$CH$_3$); 1.57 (bp, 2H, —COCH$_2$CH$_2$—); 1.96 (m, 4H, —CH$_2$CH=CHCH$_2$—); 2.25 (t, 2H, —HNCOCH$_2$—); 2.74 (t, 2H, —CH=CHCH$_2$CH=CH—); 3.69 (bp, 2H, —OCOCH$_2$NH$_2$) 4.01 (d, 2H, —OCOCH$_2$NHCO—); 4.19 (q, 2H, —OCH$_2$CH$_3$); 5.31 (bp, 2H, —CH=CH—). |

TABLE 3-continued

Chemical shifts of the raw products after washing with water

| PRODUCT | 1H NMR δ |
|---|---|
| Raw material from oleic acid | 0.85 (t, 3H, —CH$_3$); 1.24-1.27 (bp, nH, —(CH$_2$)$_n$ and —OCH$_2$CH$_3$); 1.57 (bp, 2H, —COCH$_2$CH$_2$—); 1.97 (m, 4H, —CH$_2$CH=CHCH$_2$—); 2.26 (t, 2H, —HNCOCH$_2$—); 2.74 (t, 2H, —CH=CHCH$_2$CH=CH—); 3.68 (m, 2H, —OCOCH$_2$NH$_2$); 4.01 (d, 2H, —OCOCH$_2$NHCO—); 4.19 (q, 2H, —OCH$_2$CH$_3$); 5.31 (bp, 2H, —CH=CH—); 9.26 (s, 1H, —COOH). |
| Raw material from linoleic acid | 0.59 (t, 3H, —CH$_3$); 1.19-1.27 (bp, nH, —(CH$_2$)$_n$ and —OCH$_2$CH$_3$); 1.55 (bp, 2H, —COCH$_2$CH$_2$—); 1.94 (bp, 2H, —COCH$_2$CH$_2$—) 2.02 (m, 4H, —CH$_2$CH=CHCH$_2$—); 2.25 (t, 2H, —HNCOCH$_2$—); 2.74 (t, 2H, —CH=CHCH$_2$CH=CH—); 3.70 (q, 2H, —OCH$_2$CH$_3$); 4.00 (d, 2H, —OCOCH$_2$NHCO—); 4.20 (q, 2H, —OCH$_2$CH$_3$); 5.32 (bp, 2H, —CH=CH—). |
| Raw material from stearic acid | 0.86 (t, 3H, —CH$_3$); 1.15-1.32 (bp, nH, —(CH$_2$)$_n$ and —OCH$_2$CH$_3$); 1.61 (bp, 2H, —COCH$_2$CH$_2$—); 2.22 (t, 2H, —HNCOCH$_2$—); 2.33 (t, 2H, —OHCOCH$_2$—); 3.97 (d, 2H, —CH$_2$NHCOCH$_2$NHCO—); 4.02 (d, 2H, —OCOCH$_2$NHCO—); 4.21 (q, 2H, —OCH$_2$CH$_3$); 5.90 (bp, 1H, NH); 6.12 (bp, 1H, NH). |
| Raw material from olive oil | 0.85 (t, 3H, 3X—CH$_3$); 1.18-1.38 (bp, nH, —(CH$_2$)$_n$ and —OCH$_2$CH$_3$); 1.60 (bp, 2H, —COCH$_2$CH$_2$—); 1.98 (m, 4H, —CH$_2$CH=CHCH$_2$—); 2.22 (t, 2H, —HNCOCH$_2$—); 2.30 (t, 2H, —OHCOCH$_2$—); 2.74 (t, 2H, —CH=CHCH$_2$CH=CH—); 3.70 (d, 2H, —CH$_2$OH); 4.01 (d, 2H, —OCOCH$_2$NHCO—); 4.13-4.27 (dd, 4H, —CH$_2$OCHOCH$_2$O—); 4.20 (q, 2H, —OCH$_2$CH$_3$); 5.23 (m, 1H, CH$_2$OCHOCH$_2$O—); 5.31 (m, 2H, —CH=CH—); 5.95 (bp, 1H, —NH—). |
| Raw material from rice bran oil | 0.83 (t, 3H, 3X—CH$_3$); 1.18-1.38 (bp, nH, —(CH$_2$)n and —OCH$_2$CH$_3$); 1.57 (bp, 2H, —COCH$_2$CH$_2$—); 1.98 (bp, 4H, —CH$_2$CH=CHCH$_2$—); 2.21 (t, 2H, —HNCOCH$_2$—); 2.28 (t, 2H, —OHCOCH$_2$—); 2.74 (t, 2H, —CH=CHCH$_2$CH=CH—); 3.70 (d, 2H, —CH$_2$OH); 3.99 (d, 2H, —OCOCH$_2$NHCO—); 4.11-4.27 (dd, 4H, —CH$_2$OCHOCH$_2$O—); 4.16 (q, 2H, —OCH$_2$CH$_3$); 5.22 (m, 1H, CH$_2$OCHOCH$_2$O—); 5.30 (m, 2H, —CH=CH—); 6.01 (bp, 1H, —NH—). |
| Raw material from buriti oil | 0.85 (t, 3H, 3X—CH$_3$); 1.28 (bp, 2H, —(CH$_2$—)$_n$ and —OCH$_2$CH$_3$); 1.60 (bp, 2H, —COCH$_2$CH$_2$—); 2.00 (m, 4H, —CH$_2$CH=CHCH$_2$—); 2.20 (t, 2H, —HNCOCH$_2$—); 2.29 (t, 2H, —OHCOCH$_2$—); 2.73 (t, 2H, —CH=CHCH$_2$CH=CH—); 3.70(d, 2H, —CH$_2$OH); 4.00 (d, 2H, —OCOCH$_2$NHCO—); 4.05-4.15 (dd, q, 4H, 2H —CH$_2$OCHOCH$_2$O—, —OCH$_2$CH$_3$); 4.21 (q, 2H, —OCH$_2$CH$_3$); 5.22 (m, 1H, —CH$_2$OCHOCH$_2$O—); 5.32 (m, 2H, —CH=CH—); 6.05 (bp, 1H, NH). |
| Raw material from coffee oil | 0.80 (t, 3H, 3X—CH$_3$); 1.12-1.36 (bp, nH, —(CH$_2$)$_n$ and —OCH$_2$CH$_3$); 1.54 (bp, 2H, —COCH$_2$CH$_2$—); 1.98 (bp, 4H, —CH$_2$CH=CHCH$_2$—); 2.20 (t, 2H, —HNCOCH$_2$—); 2.24 (t, 2H, —OHCOCH$_2$—); 2.71 (t, 2H, —CH=CHCH$_2$CH=CH—); 3.70 (d, 2H, —CH$_2$OH); 3.95 (d, 2H, —OCOCH$_2$NHCO—); 4.08-4.23 (dd, 4H, —CH$_2$OCHOCH$_2$O—); 4.15 (q, 2H, —OCH$_2$CH$_3$); 5.21 (m, 1H, CH$_2$OCHOCH$_2$O—); 5.28 (m, 2H, —CH=CH—); 6.12 (bp, 1H, NH). |

The invention claimed is:

1. A method of increasing the Sun Protection Factor (SPF) of a cosmetic product comprising a sun filter, the method comprising adding to the cosmetic product a lipo-amino acid alkyl ester obtained in the absence of organic solvents, and by irradiating a mixture comprising (a) an amino acid alkyl ester and (b) a free fatty acid, an esterified fatty acid, a vegetable oil, or a vegetable butter, with microwaves to obtain the lipo-amino acid alkyl ester.

2. The method according to claim 1, wherein said alkyl ester is a linear or branched $C_1$-$C_{24}$ alkyl ester.

3. The method according to claim 1, wherein said lipo-amino acid comprises an acyl group of a linear or branched, saturated or unsaturated, $C_4$-$C_{24}$ aliphatic monocarboxylic acid.

4. The method according to claim 1, wherein said alkyl ester is a $C_1$-$C_4$ ester.

5. The method according to claim 1, wherein said alkyl ester is a $C_2$ ester.

6. The method according to claim 1, wherein said lipo-amino acid comprises the glycine structure.

7. The method according to claim 1, wherein the lipo-amino acid alkyl ester is present in the cosmetic product in an amount between 0.5 and 20% by weight.

8. The method according to claim 1, wherein the sun filter is present in the cosmetic product in an amount between 5 and 80% by weight.

9. The method according to claim 1, wherein the weight ratio of the lipo-amino acid alkyl ester to the sun filter in the cosmetic product is between 1:0.2 and 1:8.

10. The method according to claim 1, wherein said sun filter is selected from cinnamates, triazines, benzimidazoles, benzylidene camphor, benzoxazoles, diarylbutadienes, phenyl benzotriazoles, benzylidene malonates, benzal malonates, salicylates, benzoates, benzophenones, dibenzoylmethanes, diphenyl acrylates, anthranilates, metal oxides, mixtures of metal oxides with lipids, and derivatives thereof.

11. The method according to claim 1, wherein said cosmetic product is selected from: skin care products, beauty masks, foundation, powders, talcum powders, soaps, perfumes, eau de toilette, eau de Cologne, preparations for baths and showers, depilation products, deodorants, antiperspirants, hair dyes, hair-waving, -straightening and -fixing products, hair-set products, hair-cleaning products, products to keep hair in shape, hair-styling products, shaving products, make-up products and make-up-removing products, products intended to be applied on lips, nail care products and nail polishes, sun products, self-tanning products, skin-lightening products and anti-wrinkle products.

\* \* \* \* \*